United States Patent [19]
Karlson

[11] Patent Number: 4,988,484
[45] Date of Patent: Jan. 29, 1991

[54] HIGH EFFICIENCY OZONE GENERATOR FOR STERILIZING, BLEACHING AND THE LIKE

[76] Inventor: Eskil L. Karlson, 4634 State St., Erie, Pa. 16509

[21] Appl. No.: 518,313

[22] Filed: May 7, 1990

Related U.S. Application Data
[63] Continuation of Ser. No. 155,067, Jan. 29, 1988, abandoned.

[51] Int. Cl.⁵ .................... B01J 19/08; B01J 19/12
[52] U.S. Cl. .................... 422/186.19; 422/186.07; 422/186.18; 422/186.2; 422/907
[58] Field of Search ............ 422/186.18, 186.19, 422/186.2, 186.07, 907

[56] References Cited

U.S. PATENT DOCUMENTS

| | | | |
|---|---|---|---|
| 1,579,162 | 3/1926 | Starke et al. | 422/186.19 |
| 2,936,279 | 5/1960 | Rindtorff et al. | 422/186.15 |
| 3,010,892 | 11/1961 | Axt | 422/186.2 |
| 3,023,155 | 2/1962 | Castor | 422/186.18 |
| 3,766,051 | 10/1973 | Bollky | 422/186.19 |
| 3,899,685 | 8/1975 | Francis et al. | 422/186.19 |
| 4,013,567 | 3/1977 | Emelyanor et al. | 422/186.19 |
| 4,025,441 | 5/1977 | Tabata et al. | 422/186.19 |
| 4,051,045 | 9/1977 | Yamamoto et al. | 422/186.16 |
| 4,079,260 | 3/1978 | Dmitriev et al. | 422/186.19 |
| 4,234,800 | 11/1980 | Kenly, V et al. | 422/186.19 |
| 4,666,679 | 5/1987 | Masuda et al. | 422/186.2 |

Primary Examiner—John S. Maples
Assistant Examiner—Philip Tucker

[57] ABSTRACT

An ozone generator for producing ozone at pressures of up to 10,000 psi from oxygen or oxygen containing gas, which contains two electrodes for forming a corona discharge through the input gas, the first electrode being cooled by a first cooling fluid and the second electrode being cooled by a second cooling fluid, which further contains flexible barrier means for equalizing the pressure between the cooling fluids and the input gas.

16 Claims, 9 Drawing Sheets

HIGH EFFICIENCY OZONE GENERATOR FOR STERILIZING, BLEACHING AND THE LIKE

This invention is an ozone generation system that teaches the method to employ very high pressure within the generator to produce ozone using less energy, up to 50% less, dependent on pressure and temperature, than a system operating at ambient temperature and pressure. Also, as part of this invention, there are examples of how and where this generator can be used and a method to control these systems and the generator.

An example of a water purification system is shown which teaches not only how to use the new economical ozone generator but this system also teaches how to produce ultra pure water and a method to stop any outside contamination of the purification system before a new sample is taken. A second example shows a sterilization system that could employ the high pressure ozone generator. This system is the upgraded "Karlson" Ozone Sterilization System" which is unique in that its catalyst which destroys the ozone before any gas exits also; controls the rate of ozone the ozone generator produces thus setting the concentration of ozone that is employed as the sterilization agent in the sterilizer. This control is accomplished by measuring the heat the ozone catalyst is producing from used exit gases during the steriliziation cycle. A third example of using the high pressure ozone generation system is employing it in the bleaching of wood pulp. The ozone catalyst will be used in two ways in the pulp system in the bleaching operation. The catalyst will convert the ozone to oxygen before it leaves to the outside air and the heat produced in the catalizer, by the ozone conversion to oxygen will be used as a measure of how much ozone is left in the off gas and how much more is needed for the most efficient bleaching action. The control computer will be sent data from the catalyst and the flow meters measurement in order that it can compute and set the ozone generator for a particular batch size to produce the most efficient amount of ozone to bleach the pump most economically.

In drawing, FIG. 1 is a basic diagram of a corona discharge ozone generating system using air or oxygen at atmospheric pressure.

Figure 1:
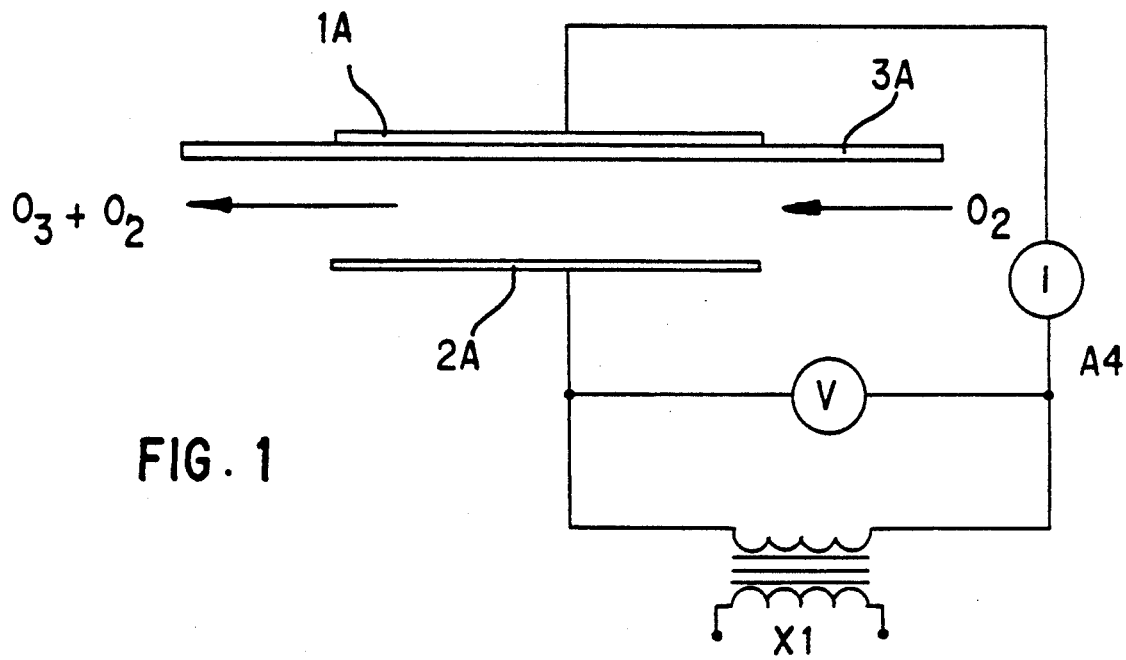
Figure 2:
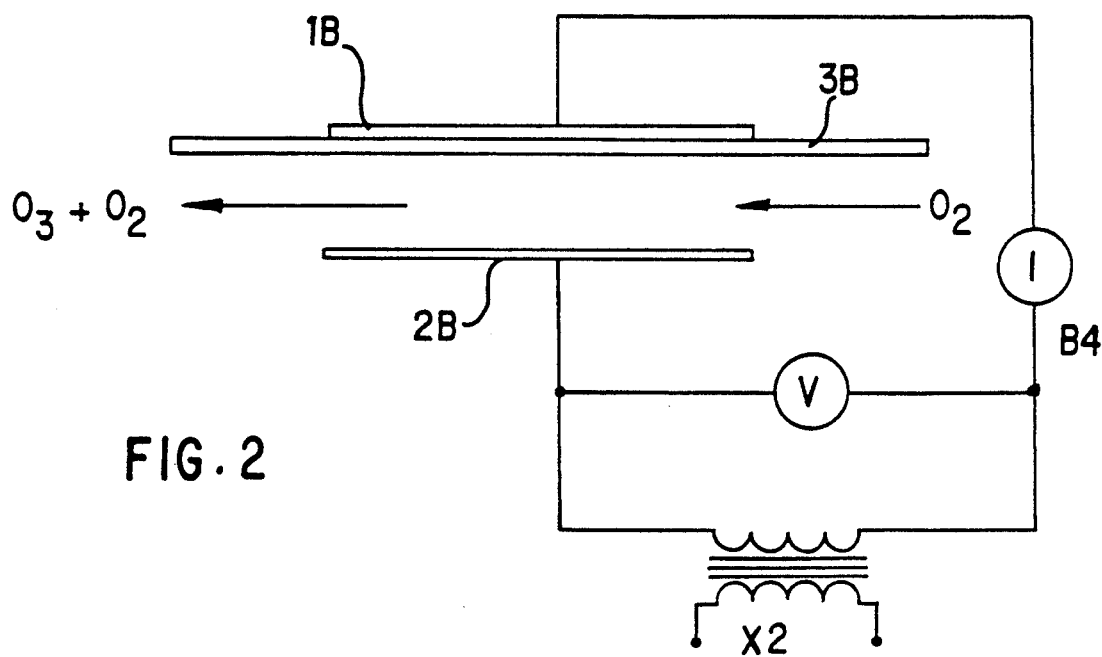
FIG. 2 is a basic diagram of a basic corona discharge ozone generating system using oxygen at pressures of 3,000 pounds per square inch.

In the corona discharge ozone generating system of FIG. 1 is a diagram of a high alternating voltage, for example 10 Kv at 400 Hz, the transformer is connected across a metal electrode 1a and a metal electrode 2a plated on a dielectric such as glass 3a. Oxygen at atmospheric pressure flows through the space between the glass and the electrodes 1a and 2a. The voltage is sufficiently high to cause ionization of the oxygen but is below the value at which break down and sparking occurs. The power consumed in the ozone generation is indicated by an ammeter 4a. FIG. 2 shows the same apparatus of FIG. 1 supplied with oxygen under a pressure of 3,000 pounds per square inch. By lowering the voltage applied across the electrodes 1b, 2b until the current indicated by ammeter 4b is the same as previously noted 4a when the apparatus was supplied with oxygen at atmospheric pressure, the ozone output is greater than the output from the atmospheric pressure oxygen.

The lower voltage indicates that the power required for ozone generation is decreased by the increased operating pressure. This has been tested for oxygen pressures of 500 pounds to 3,000 pounds per square inch. It was found the higher the pressure the greater the yield of ozone. There is no reason why the same results should not be obtained with oxygen pressures above 3,000 pounds per inch.

The advantage of having a high pressure oxygen in the corona area, where the ozone is being produced, is that without changing any other parameters more ozone is produced per watt hour. At high pressure, the flow rate of oxygen must be increased, otherwise, the corona will act to destroy the ozone it generated. The temperature of the glass insulator also increases when the gas pressure is increased. The reason for this temperature increase is that more energy has passed through the glass and resistance across the high pressure gas area is lower. The advantage is that the glass insulator dielectric has not changed and its ac resistance remains nearly the same. In practice the high voltage was lowered to the same current level as when operating at low gas pressure, and the system used less energy in watts, but produced more ozone.

Figure 3:
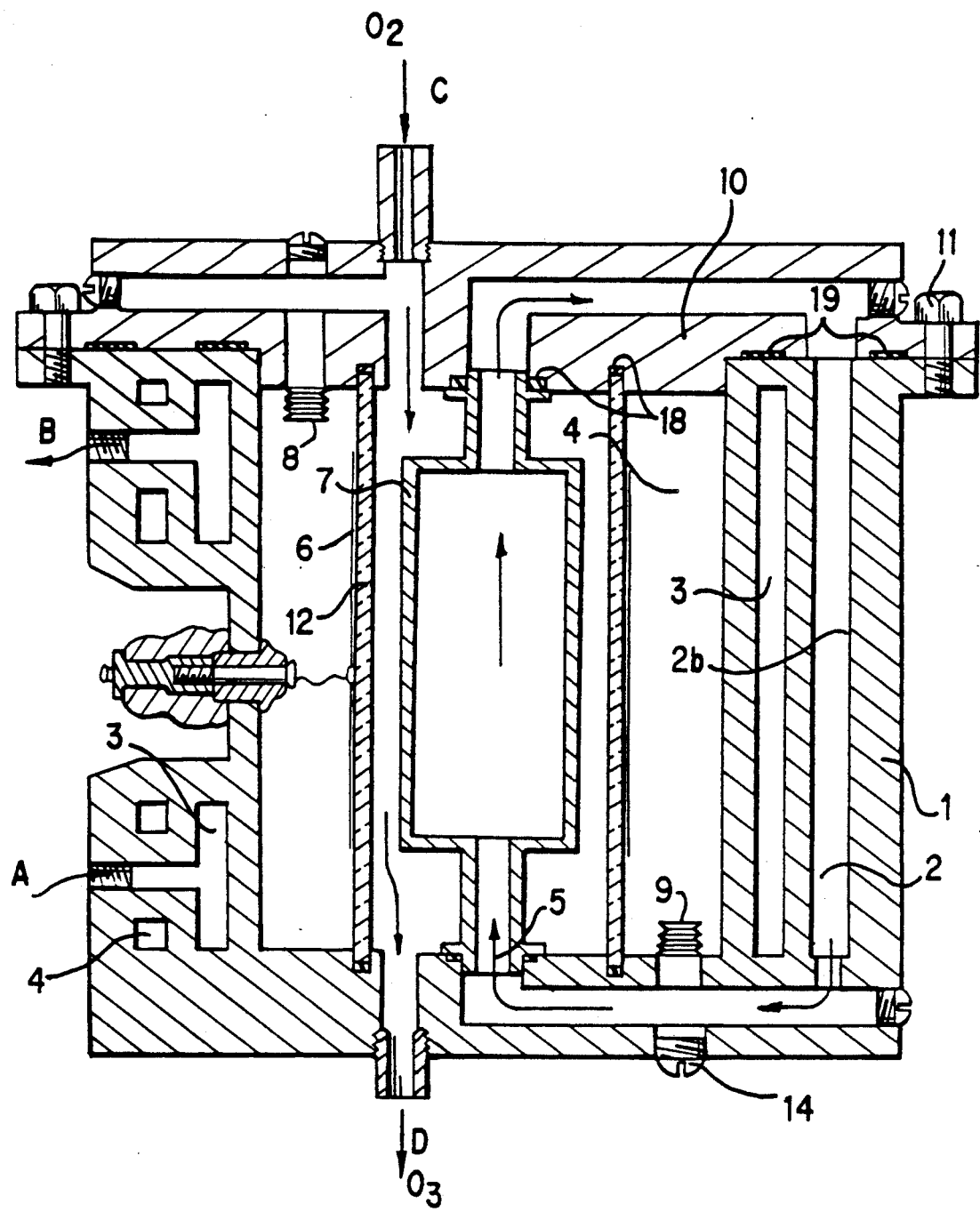
FIG. 3 is a sectional elevation of an ozone generator using oxygen at pressures of 3,000 pounds per square inch.

FIG. 3 is a center cut slice view of the internal structure of the high pressure ozone generator. This generator is made up of four major members, container 1, cover 10, glass or ceramic insulator 12, and inner metal electrode 7.

The outside container 1 is made up of three cooling compartments 2, 3, 4. Compartments 2 and 4 are hermetically sealed and filled with incompressible liquids. Compartment 2 is filled with water which cools the center or ground electrode 7 by conduction and convection—the hot water leaves the center electrode by rising up through the end plate 10, down through cannel 2b and after being cooled, it rises back going up through 5 into the center electrode. For increased cooling a sealed pump can be added in line 2b.

The second cooling compartment 3 extracts the heat from both the sealed internal cooling water of compartment 2 and the sealed inner oil of compartment 4. The inner oil compartment 4 cools and insulates the glass tube 12 which is plated with silver over a portion of its external surface to provide high voltage electrode 6 next to the oil.

The cooling water for chamber 3 enters at point A, exits at point B. This cooling chamber lies between the oil cooling and the water cooling chambers 4 and 2. This cooling water, cools both the oil which controls the temperature of the glass insulation tube 12 and the water which controls the temperature of the center ground electrode 7.

The container part 1 also has welded to its bottom a pressure equalizer bellows 9. This equalizer sets the water pressure in the ground electrode cooling loop 2 at the same pressure as the oil pressure in the oil cooling chamber 4 for the high voltage electrode 6.

The second part 10, the cover, is held to part 1 by a ring of screws 11 around its edge as is shown in FIG. 3. The two high pressure metal rings of packing 19 seal the top 10 to the container 1. The cover 10 also aligns both the glass insulator 12 and the center electrode 7.

The cover end plate 10 also has attached to it, projecting into the oil 4, down from cover 10 a pressure equalizer bellows 8 which transmits the pressure of the high pressure oxygen to the oil. The pressure equalizers 8 and 9 are each made of a bellows of thin nickel welded to the top plate 10 and the bottom of the tank 1. As the pressure is increased, the oxygen builds upcoming in at point C (in the cover 10) both 8 and 9 will equalize the pressure without mixing of water, oxygen and oil. The pressure across the glass insulator will never be more than one pound no matter what the input oxygen pressure at point C is. In all cases both the water and oil hermetically sealed cooling systems must be full with little or no air in either system.

The third part 12, the glass insulator, is mounted in grooves in both the top cover 10 and the bottom of the container 1. Sealing is accomplished by a neoprene rubber ring coated with floura carbon grease 18 at either end of the tube as shown in FIG. 3. This seal must be able to stand ozone at concentrations up to 12%. It is important to note that by using the pressure equalizer less leak problems will occur since there is very little pressure across any of the seals except at 19. The glass tube 12 has a coating of silver plate 6 over its outer sides except for a clear area of two inches at either end. The silver is attached to a wire that leads to the center conductor of insulator 20. The high voltage source is attached to this point. The case 1 is grounded. The inner metal electrode 7, the fourth member, is mounted between the top plate 10 and the bottom of container 1 as shown in FIG. 3. "0" rings 18 seal both ends.

Generating the ozone at high pressures is more efficient —produces more grams of ozone per watt. In U.S. Pat. No. 3,719,017, ozone and air or oxygen mixture were compressed for spraying at pressures of up to 1,000 pounds per square inch. It has been learned ozone can be used more efficiently at high pressures only if it is generated at high pressures. The heat of compression obtained when pumping an ozone gas mixture to a high pressure will destroy nearly all the ozone to a gas not usable for sterilization. Another advantage of producing ozone at high pressure is that when you release it to a lower pressure as it will get colder and will be active longer.

Figure 5:
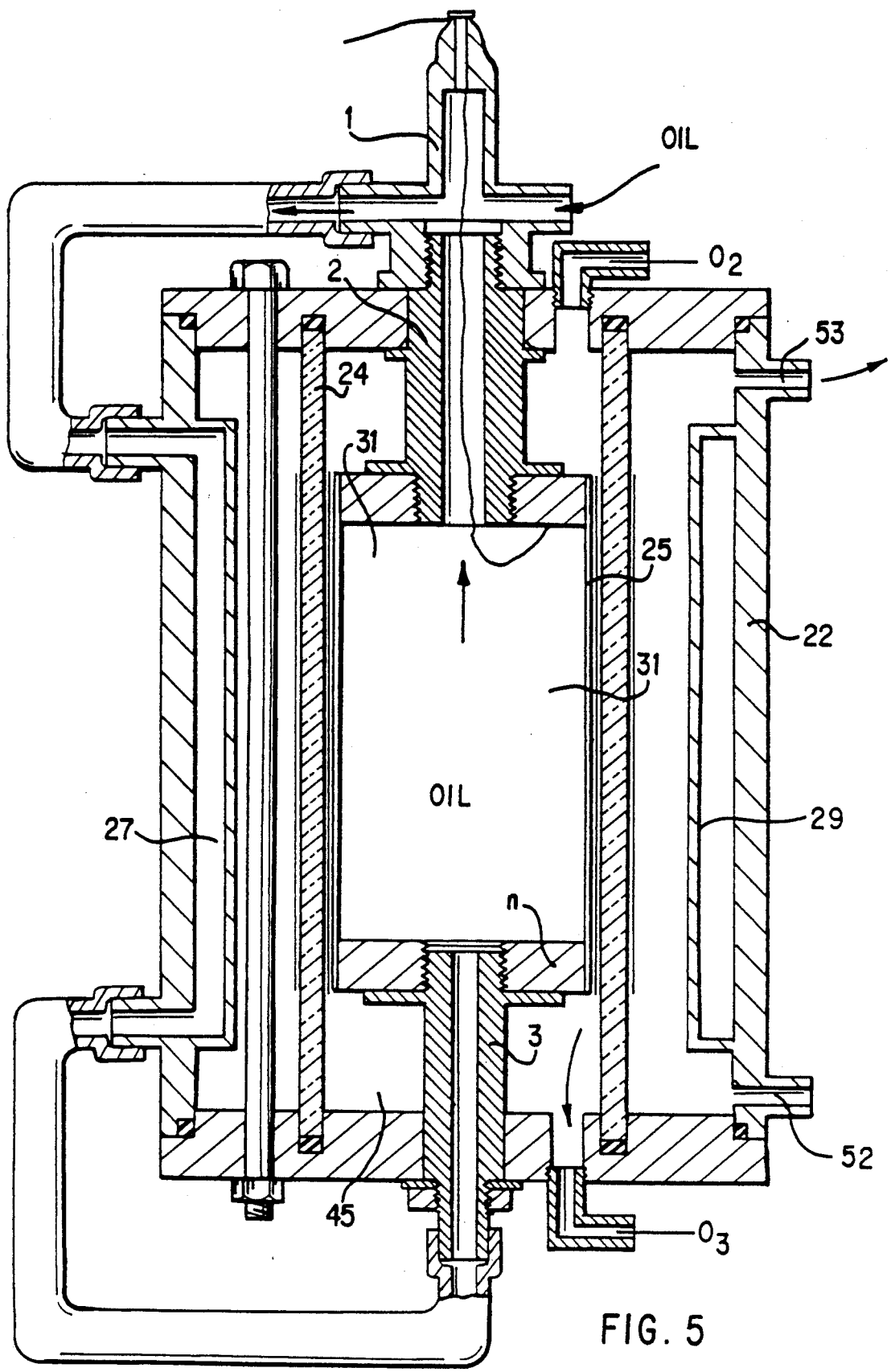
FIG. 5 is a section through a modification of the high pressure ozone generator.

The ozone generator design shown in FIG. 5 has a number of parts: The metal, outer shell 22 encases the ozonator and carries on its inner surface a heat exchanger 27, 29 to cool the oil 31 which cools the inner electrode 25 and through the electrode cools the oxygen and ozone as they pass between the inner electrode and the glass insulator 24.

The oil is cooled by convection up through the inner electrode and down through heat exchanger 27. A pump could be attached in line at 37 to increase the flow rate and increase the cooling of oil from 31.

The plastic molding 32 at the top of the ozone generator serves several purposes: It supports the upper end of the inner insulator "Q" which is attached to 35 the metal ring holding 25 in place. Plastic element 32 also provides a passage for the flow by thermal convection of the heated oil out of the inner electrode to a high pressure plastic tube 36 on the way to the heat exchanger back through tube 37 and on to plastic molding 38, which returns the oil to the inside of inner electrode 25. Parts 32, "Q" and 38 are all produced of high strength filled teflon. Nut 40 over washer 41 holds teflon tube 38 in place in lower end plate 42.

Two O-rings 43 are used at each end of the ozone generator to provide a seal between the cooling water space 44 and the gas space 45, support and protect the glass insulator 24 which has a conductive coating 46 on its outer surface to serve as the outer electrode. Two more 0-rings 43 seal the outer shell 22 to the top plate 47 and the bottom plate 42 to prevent leakage of the cooling water 44. The complete unit is held together by a ring of six through-bolts 49, which also provide pressure on O-rings 43 to assure leak-proof seals.

In operation, air or oxygen is pumped into the unit through inlet fitting 50 and then passes through a corona discharge between inner electrode 25 and insulator 24 where ozone is formed in "P" area. The resulting oxygen/ozone mixture is discharged from the unit through fitting 51 at the bottom of the unit. The cooling water enters at point 52 and exits at 53.

The advantage of FIG. 5 ozone generator is that the outside 22 is at ground potential and glass insulator 24 is water cooled and its outer surface next to the cooling water is also at ground potential. The use of water as a cooling agent for the glass is more effective than oil. The ozone generator in FIG. 5 can also be built to operate at high pressures by using the same method as was used in FIG. 3. It would only be necessary to design the full system to stand 3,000 pounds and inserting an equalizing bellows in part "N" in the inner electrode in FIG. 5 and also adding an equalizing bellows in the wall at 29 between the oil and cooling water. The cooling water for a high pressure system would be a closed system having the water pumped from 53 in FIG. 5 to a heat exchanger (not shown) back to 52. No air should be left in the water cooling system. This cooling system must be designed to stand the same pressure as the oxygen that is fed to the ozone generator. The water and oil pressure is now equalized with the rest of the system as for FIG. 5 ozone generator.

Figure 7:
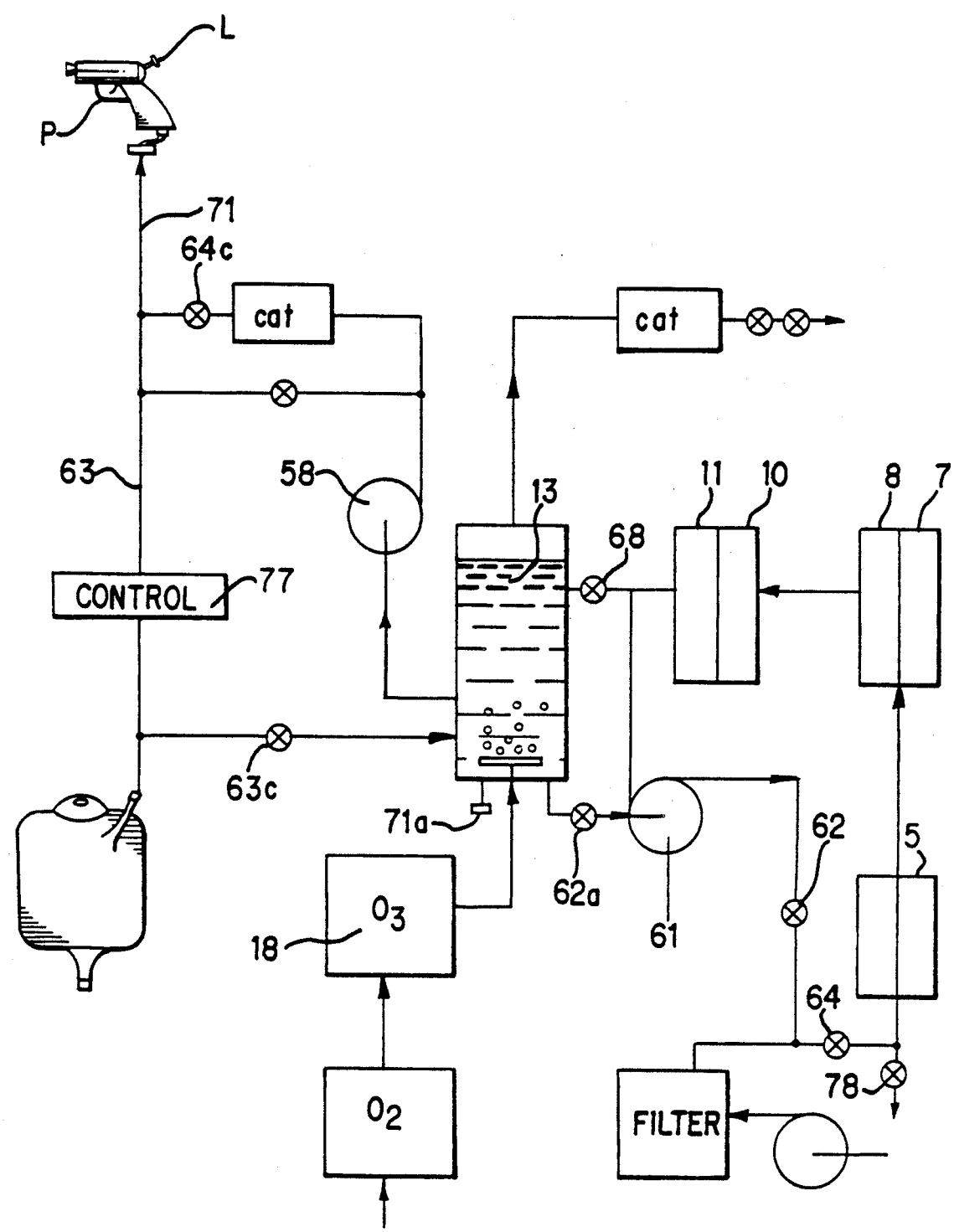
FIG. 7 is a diagram of a system for producing hospital grade pyrogen free water.

This ultra-pure water generating system of FIG. 7 can dispense water by either of two methods:

First, the unit can dispense either ozone-free water or water containing 5 ppm of dissolved ozone, depending on the application. Ozone free water passes through catalyst 64A which converts the dissolved ozone to oxygen.

Figure 4:
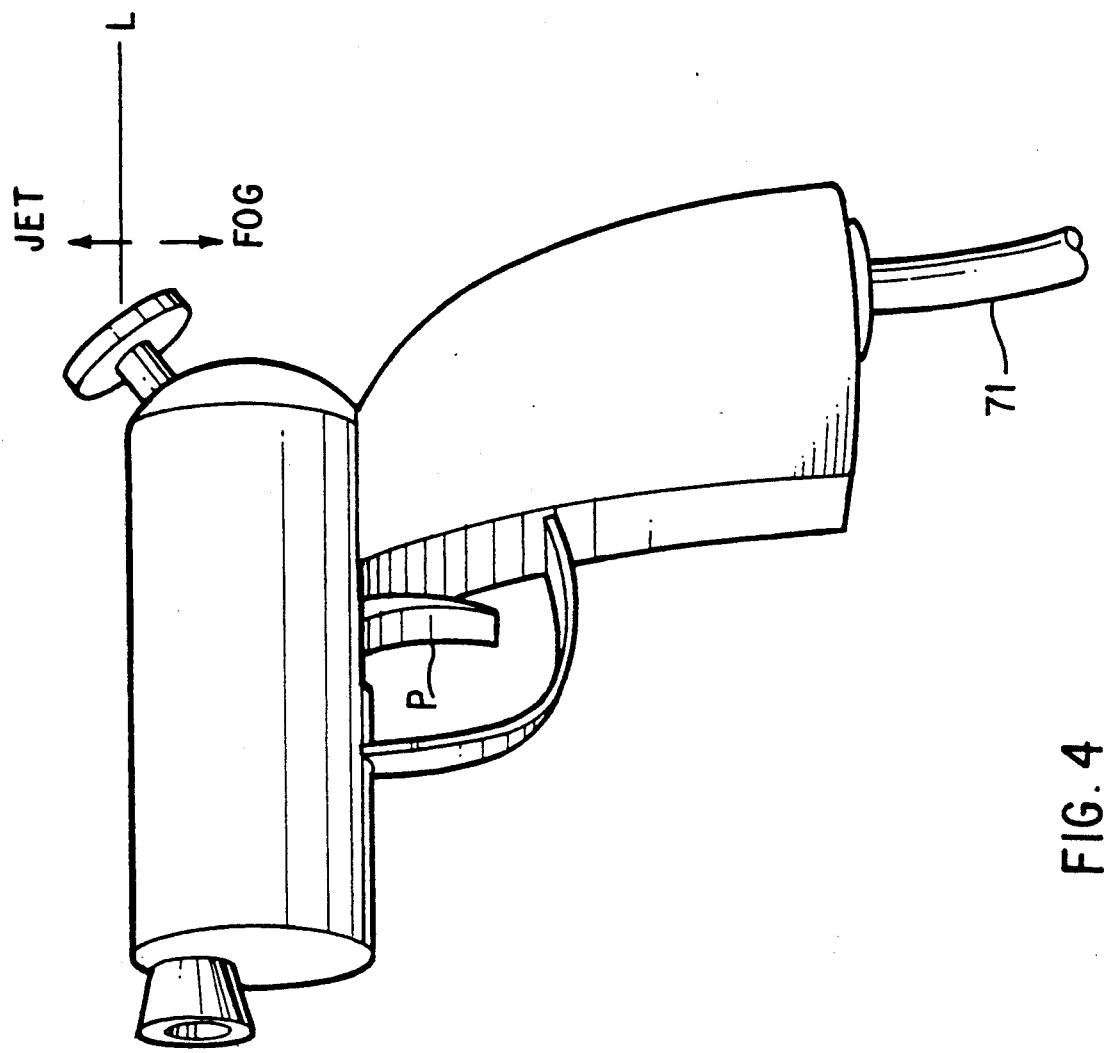
FIG. 4 is a view of a spray gun for pyrogen free water to be used in hospital emergency rooms.

When water is needed in the emergency room, the dispensing hose 71 is disconnected from the recirculating port 71A and connected to the applicator spray head 72 at 71B as shown in FIG. 7. Details of this spray head are shown in FIG. 4. A thumb control L on the spray head 72 varies the output from a compact jet to a fine mist, while the pressure is controlled by the operator's finger at P. In this manner, a wound can be washed with either pure, sterile water, or sterile water containing dissolved ozone, which will act as an anocyte.

The system of FIG. 7 will produce sterile water, free of dissolved solids and gases, suspended particles and pyrogens. The input water can come from any source. The input, contaminated water, is first pumped through a series of graded particle filters 3, to remove all suspended solids down to 0.1 micron. The water will next be forced through a membrane filter to remove particles from 0.1 micron down to dissolved solids larger than 10,000 Daltons molecular weight. This relatively pure water still contains some dissolved solids and gases. To extract the remaining solutes, the water is next passed successively through anion and cation exchange columns 5, 7. An organic filter 8 such as activated carbon and a mixed-resin (anion and cation) 10 exchange column. Finally, the water is sent through a fine-particle filter 11 to remove any particles which might have been dislodged from the ion-exchange resins or the activated carbon. At this point, the purified water is sent to a storage tank 13—of approximately 10 gallons capacity—where it is polished by dissolved ozone. The water is stored in this tank for later use in a hospital, either to fill plastic containers, to make up i.v. drug prescriptions or electrolyte solutions or for washing wounds in the emergency room.

The raw water as shown in FIG. 7 is first pumped by pump 56 through a series 3 of graded particle filters including a filter which will collect particles down to a 1.0 micron, followed by a second particle filter which collects all remaining particles down to 0.1 micron and finally through a fine membrane filter which collects all particles or molecules larger than 10,000 Daltons. In areas where the water is polluted with oils or sludge, the input pump is supplied with a centrifugal separator 2 attached to its shaft, which separates the very heavy particles before they reach the filters 3. All filters are preferably cartridge type for ease of maintenance and the differential pressure across each one is monitored to indicate when replacement is needed.

The filtered water is still under some pressure from the supply pump 56 and is now forced through the ion-exchange columns 5, 7. These columns are both monitored for effectiveness by measuring the pH differential across each column during tests with contaminated samples, to check for exhaustion.

Next the water is passed through an organic filter 8 which may be either activated carbon or a neutral organic resin. This filter collects dissolved gases and light molecular weight, neutral organic compounds. Finally, the water is sent through a mixed-resin (anion and cation) 10 and through a particle filter 11 to collect any material which might have washed off the ion-exchange resins or the organic filter. The clean water is now sent to the storage tank 13.

The water is now in the storage tank 13 where final purification is achieved by the oxidizing action of ozone. This destroys any organisms or material which have either passed through the filtration system or have entered the unit through the discharge ports or safety valves 21. Bacteria or other air-borne contaminants could possibly enter the system when a pressure-relief valve opens, or when water is withdrawn for use or when control samples are taken at 11A, 11B or 78.

Polishing is accomplished by bubbling high concentrations of ozone—over 5% by weight—through the water in the storage tank 13. The remaining ozone is sent through a catalyst 20 (manganese oxide plus copper oxide) which converts the ozone ($O_2$) to oxygen ($O_2$) It should be noted that it has been well-established that treatment with ozone will destroy any microorganisms or pyrogens remaining in the water, as well as any other oxidizable contaminants, as mentioned earlier. The temperature at 68 of the ozone catalyst is used as a monitor of the amount of ozone manufactured and is used to control the ozone generation system at 68A.

The ozone generation system is unique, for it provides its own oxygen from the surrounding atmosphere. The raw air is first pumped through a drier and a dust filter 15. The air is then forced through an oxygen concentrator 17, similar to the units presently used in some hospitals to produce breathing oxygen. This dry, dust-free, 85% oxygen pumped by 85 to a high pressure and cooled at 85A. It is then delivered to the ozonator 18, which produces ozone efficiently at a high or low pressure using system in FIG. 5 at a concentration of over 5% by weight at a flow rate of 1 liter per minute. The oxygen/ozone mixture is bubbled through the water in the 30 liter storage tank 13, where it destroys any oxidizable foreign matter. The maximum pure water discharge rate from the storage tank is two liters per minute, so the minimum time that the water is exposed to ozone is 15 minutes. The waste ozone/oxygen mixture leaving the tank is passed through a catalyst 20 of manganese and copper oxides which converts the ozone to oxygen, before exhausting the waste gas to the surrounding air. The exhaust gas is passed through two, tandem relief valves 21 to reduce the possibility of any air-borne bacteria, dust particles or other foreign matter entering the system at that point. To guarantee no ozone is left in the exhausted gases a heater is built into the exit portion of the catalyst tube to raise the temperature of the escaping gas to 500° C. This will convert any $O_3$ left.

Figure 6:
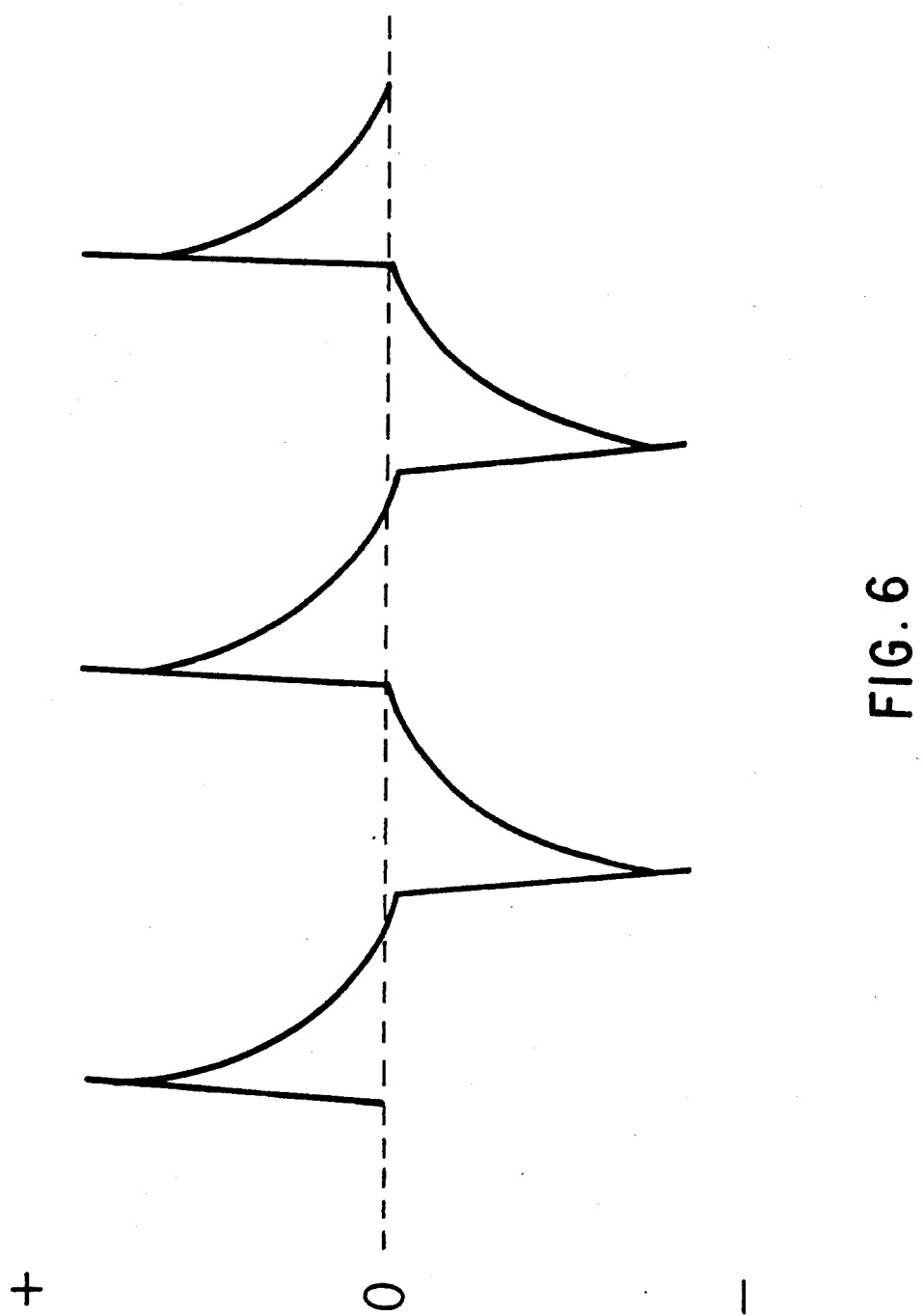
FIG. 6 is a diagram of the ozone generating electronic pulses.

The ozone generator shown in FIG. 5 is an electrostatic device. This generator is driven by a step-up transformer (output over 23 kv) which in turn is excited by a dc supply —120-160 V—which is chopped at a frequency in the range of 400 to 1500 Hz to produce a train of constant peak voltage spikes as shown in FIG. 6. The higher the spike frequency, the greater the ozone output will be.

There are a number of advantages to this new ozone generator. As shown in FIG. 5 the outer, metal shell 22 of the generator is at ground potential. The electrostatic driving system is so designed that only the 120-160 V dc supply and the high-voltage end of the step-up transformer are above ground.

The driving oscillator and the control circuits are all no more than 25 volts above ground. This system is transformer coupled to the Hi Power SCR's that chop the 120-160 Volts DC which drives the high voltage transformer. This ozone generator is water-cooled, with the water contacting the glass insulator 24 directly. The inner, stainless steel electrode 25 is oil-cooled by the oil-to-water heat exchanger 27 on the inner surface of the outer shell 22 to cool the oil. For more efficient cooling of the oil from the inner electrode 25 fins can be placed on the inner side of the 29.

Another advantage of our design is that a higher operating pressure may be used, which will produce more ozone per unit of applied energy. Since the cooling water is surrounding the glass insulator the oxygen can be supplied at a high pressure, the insulator 24 must then be loaded in compression by the cooling water at a pressure just slightly higher than oxygen pressure employed. The water pressure will counteract the pressure of the gas inside the glass insulator. The insulator will only have across it the differential pressure of the water and oxygen. An oxygen pressure of 20 atmospheres or higher can be employed as long as the cooling water is maintained at the same pressure or slightly higher. The pressure difference between the oil at 31 and the oxygen when operating with high pressure oxygen in the 45 area can be solved by adding a pressure equalizer at point "N" between the oil and the high pressure gas for the FIG. 5 ozone generator as shown in FIG. 3 at point 8 and 9. When using this technique no air can be present in the cooling oil circuit. For high pressure operation the oil and cooling water systems must be built so as *not* to move on a pressure change.

An example of the use of the efficient ozone generator in water purification system is shown in FIG. 7.

The most important but simple advantage of this ultra pure water system FIG. 7 is that after each use it goes through a self sterilization cycle. It was found that hospitals all over the world do have water purification systems but after being in use for some time they become contaminated. We have therefore produced a pure water system that sterilizes itself after each use. It has been found no matter how hard you try not to contaminate a pure water system it still will be contaminated by outside microorganisms.

After each use of the system, line 71 is plugged back into 71a. This action automatically starts the sterilization cycle (if this is not done no more water will be produced). Pump 58 and 61 both start pumping. Pump 58 forces water through 71 back into tank 13 and through line 63 back through controller 77 through 63C to 13. This action cleans both lines during this time the ozone generation system is feeding ozone to tank 13. Pump 61 is back flushing clean water through 11, 10, 8, 7 and 5 while electronic valves 68, 62 and 64 are closed and valves 62A, 69 and 78 are open. After 10 minutes of flush, valves 69 and 78 are closed and valves 62 and 84 are opened. After 10 more minutes of back flushing time at this setting, all valves are reset in operating condition and both pumps stop pumping. The ozone generation system is off and the ready light goes on. The pure water system is again ready to produce pyrogen free water.

Figure 8:
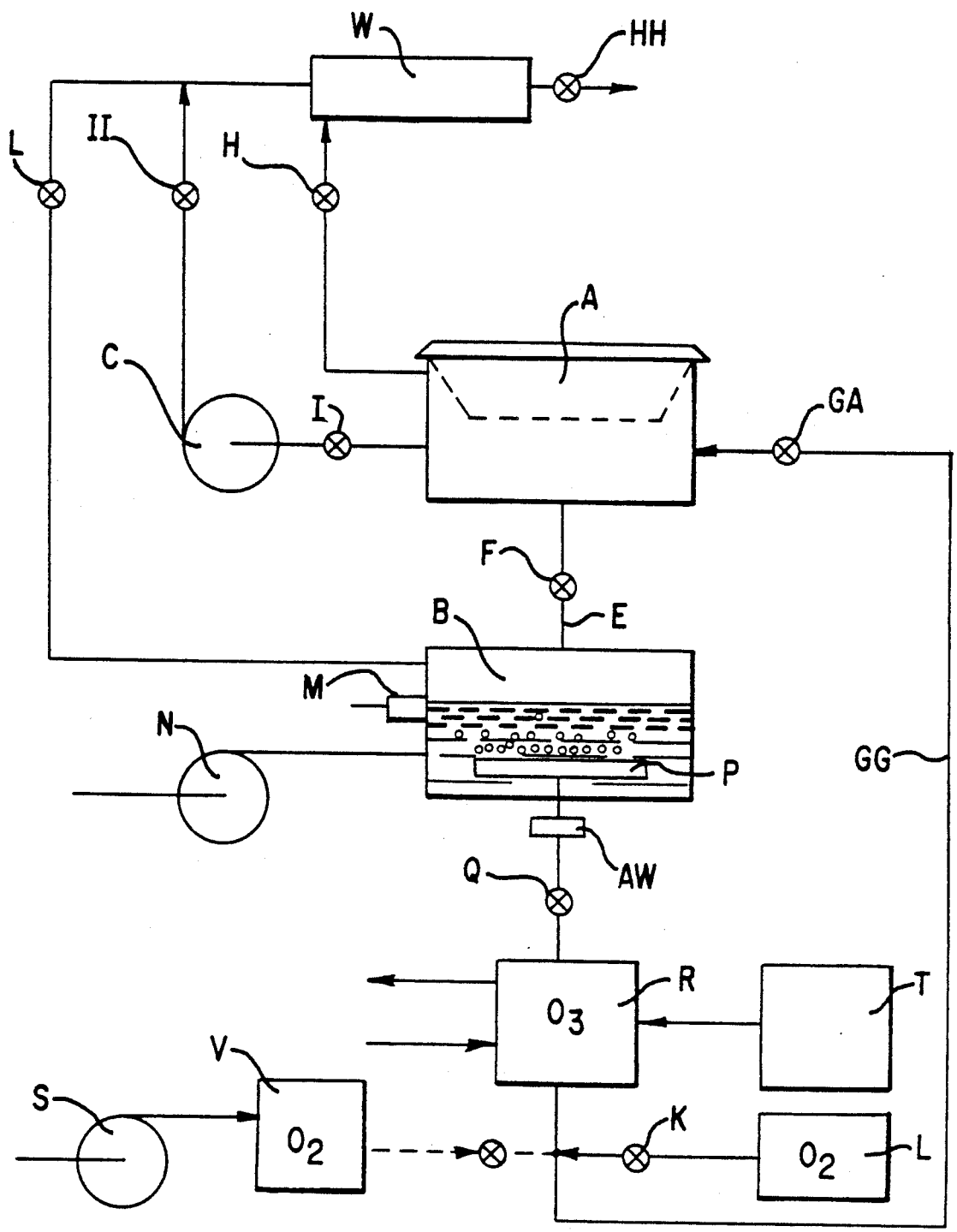
FIG. 8 is a diagram of the upgraded Karlson Sterilizer employing either bottled oxygen or oxygen generated by air extraction.

The second example of a system to use the high pressure ozone generation system is the upgraded Karlson Ozone Sterilization System, FIG. 8. This system was designed for military use to replace the Ethylene Oxide (ETO) system which is dangerous, takes too long for complete sterilization and aeration cycle.

The ETO system takes from 5 hours to a week for aeration dependent on what the item is that was sterilized. The Military Karlson Sterilizer takes less than two hours for the whole cycle with no gas leaks or health problems. This unit will use less than ½ the total energy required to operate an ETO system of equal size.

FIG. 8 describes the Karlson Field Sterilizer that was designed for military use.

The high pressure ozone generator can either receive oxygen at 2,000 to 5,000 psi from a tank L or it can get its oxygen from an oxygen extractor that is fed high pressure clean air pumped to it by pump 6. The ozone generator is cooled by outside water. It is powered from either a 110 volt 60 Hz source or it can be supplied with its own electrical generator T driven by a 1 ½ Hp gas motor. The ozone generator R is controlled by W the ozone distruct system. This catalyst W controls the ozone generation by monitoring its temperature (the higher the temperature of W, the higher concentration of ozone that is produced). Ozone of set controlled concentration leaves R through valve Q where the pressure is dropped. The gas has cooled from its expansion and its temperature is controlled by A-W. The ozone oxygen mixture then enters tank B by going through porous tube P. Minute bubbles are formed in the water in tank B. The oxygen ozone gas mixture passing through a controlled depth of water produces a gas with close to 100% humidity. The water depth is controlled by M in turn controls pump N. The pressure in tank B is controlled so that a continuous flow of gas leaves the tank through valve L, this gas is dumped into the W Catalyst. A steady flow is necessary to have a constant ozone concentration in this low pressure tank—20 to 40 psi and to monitor by W and control the ozone concentration produced at R.

After the tank A has been filled with a load of goods to be sterilized, the door is closed and latched as this is done the tank A is pumped down by pump C. That takes in the order of 5 minutes for a $1.5^3$ ft. unit. When the pressure in the sterilization tank A gets down to 1 mm pressure the pump stops, valve I is closed, valve F is opened and in rushes cold 6 % ozone and oxygen with a high humidity of 85% oxygen. This gas will enter any small space in or on the instruments to be sterilized.

After a sterilization of ½ hour the II valve is opened, the HH valve is closed and the F valve in line E is also closed. The valve L to W is closed. The pump pumps down the A sterilization tank A through W. Note: pumping is done through W so that the pump will not be injured by the ozone. The W catalyst has converted the ozone back into oxygen. As the pressure in tank A is going down the pressure in tank B is going up in pressure when it reaches 50 psi the pump C is stopped. Valve II and H are closed and valve F in line E is opened, the rush of ozone and oxygen for the second time fills tube, spaces, etc. of instrument sterilized. After the pressures have been balanced in Tank A and B valves H and HH are opened. Thirty minutes more of sterilization time is all that is necessary to complete the full sterilization cycle. At the end of the cycle, Valve F is closed, L is open, Q is still open, the high voltage is turned off, no more ozone is generated for this cycle. Valve Ga is open to let in flushed out clean oxygen from lines GG. Valve Ga reduces the pressure to not more than 30 psi—gas is flushing the sterilization tank for five minutes. This gas is also dumped into W through Valve H. The advantage of this sterilizer is that it is faster than the ETO system and does not need anything but water in order to operate as a portable instrument.

The third example of using the high pressure (2000–5000 pound per square inch) ozone generation system, is in a bleaching system for the wood pulping industry. The cost of each pound of ozone for bleaching with our high pressure system will be less than ½ the cost of a system employing oxygen pressure in the 15 psi range. This cost maybe found to be less than the present cost of chlorine.

Figure 9:
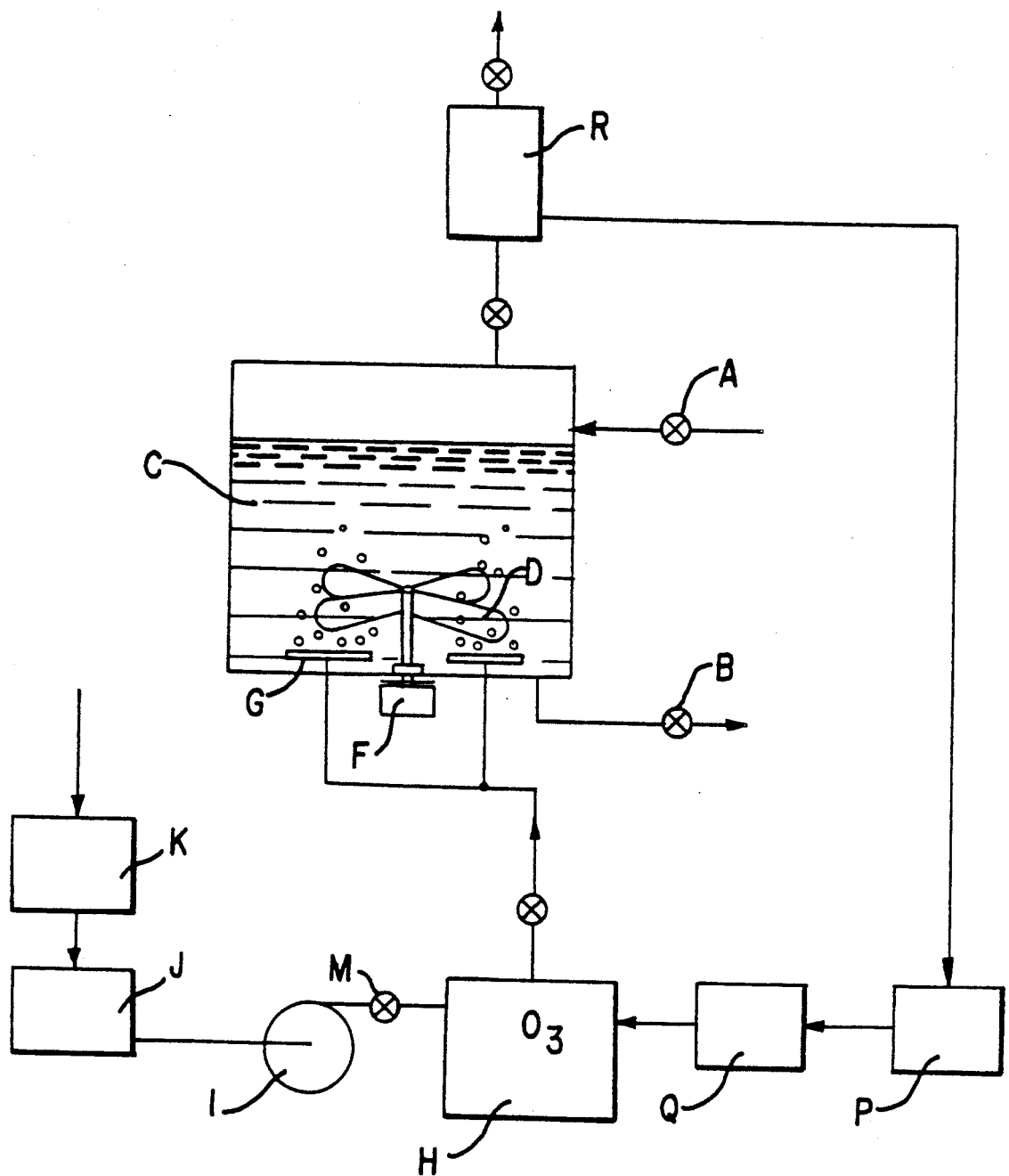
FIG. 9 is a diagram of a proposed pulp bleacher employing ozone generated by the high pressure system shown in FIG. 3.

FIG. 9 is a diagram of the use of a high pressure ozone generation system for the bleaching of wood pulp. The wood pulp is pumped into tank C through A and pumped out through line B when the bleaching is complete. This is a batch method system but could be developed to be a continuous system. Mixer D is driven by motor F. Fine bubbles of high ozone concentration are emitted from defuser G in tank C. The finer these bubbles are the more activity will be produced. K is the air filter dryer and pump. The dry, clean air is forced by pump at K through the oxygen extractor J which converts room air into 85 to 90% oxygen. This oxygen is pumped up to 2000 to 5000 psi by pump I through control valve M into high pressure ozonator H which produces required ozone levels at a controlled oxygen flow. The production of ozone is controlled by P that get its ozone concentration data from R the ozone catalyst. The controller sets the frequency at which the high voltage input at Q is generated. This high voltage in the range of 5 to 15 Kv is pulsed in a range of 500 Hz to 1200 Hz dependent on how much ozone is required. The ozone is controlled by the temperature measure at the catalyst R. This temperature measurement sets the frequency at Q which in turn controls the ozone generator at H. In some cases it may be more economical to pump raw air to high pressures to produce ozone with instead of using bottled or extracted oxygen at high pressure.

It should also be noted that the ozone generated by high pressure ozone generator can also be employed to treat drinking water. The use of ozone to produce drinking water is not new but the price of ozone generated as shown by FIG. 3 could very well compete in price with chlorine.

Figure 10:
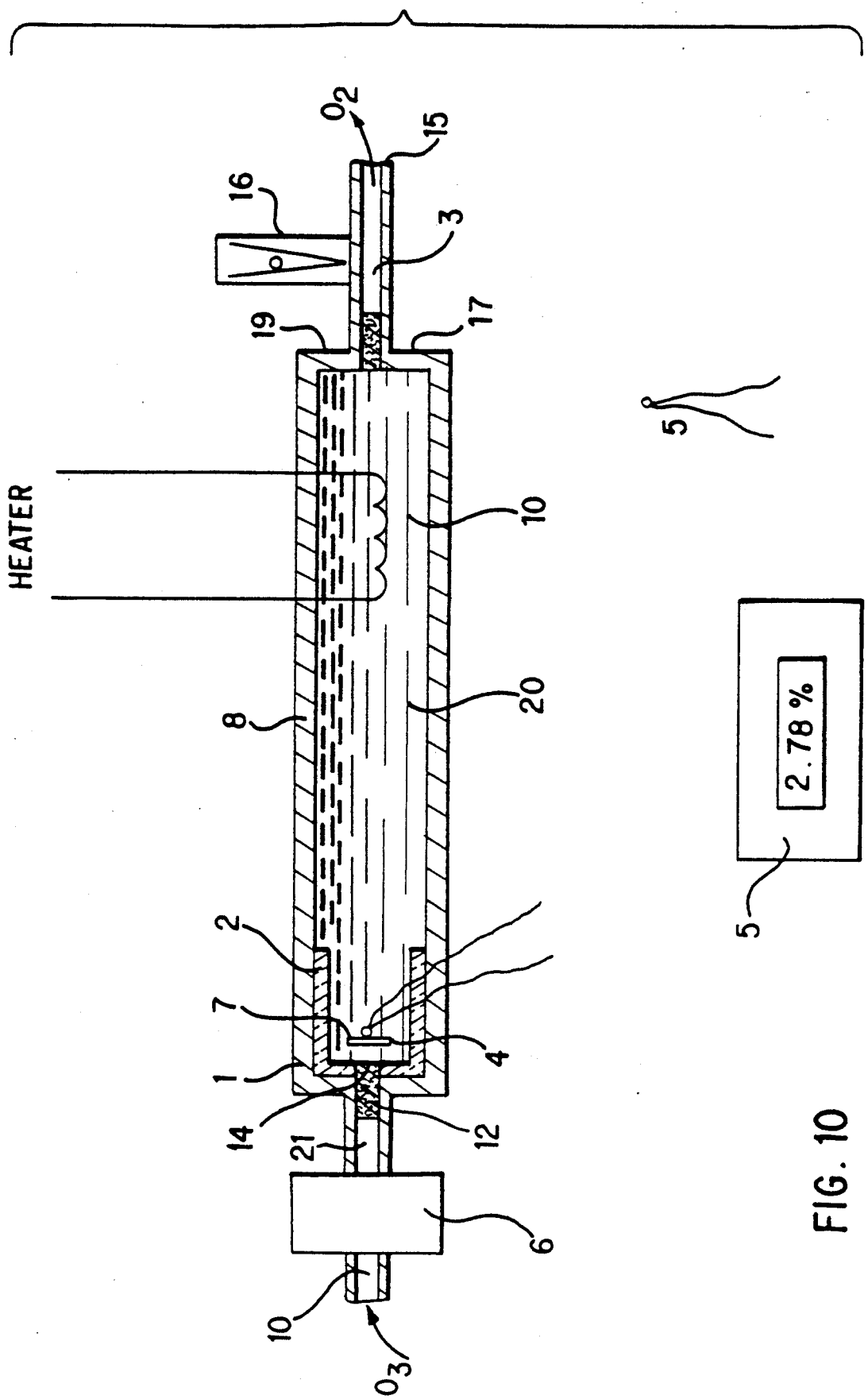
FIG. 10 is a diagram of the Ozone Catalyst and its use as an ozone control monitor and measurement instrument.

The control system employed on the three examples shown in FIG. 7, 8 and 9 are all controlling their high pressure ozone generators with a system identical to the ozone concentration control system presented in FIG. 10.

Basically the ozone monitor used in this system is a mixture of magnesium oxide and copper oxide operating as a catalyst. The catalyst is placed in a tube 24 inches long with a diameter of 3 inches, for a design that will catalyze a flow of 4 liters per minute with an ozone concentration of from 2% to 10% ozone by weight. The sizes of this catalytic system is controlled by gas flow, heat and % ozone concentration. The three examples presented in this application were in the range of from 2 to 10% ozone concentration and a flow of 1 to 6 liters per minute was used.

The tube H was 24 inches long FIG. 10 with a 3 inch diameter, at the inlet end the first 3 inches was insulated with fiber glass A and layers of asbestos B. L a plug of fiber glass at M kept the granules from leaving the pipe. The pipe H was filled with the catalyst by filling it through the O end, a thermocouple was placed in the middle of the pipe at G with a small heat sink D attached. This thermocouple measured the temperature of the first section of catalyst. This section has the greatest change in temperature with any change of flow or ozone concentration.

The gas to be measured enters F a dust filter coming through J the first temperature measurement is measured at H before the gas enters the converter at M as soon as the ozone mixture enters H in the M area the catalyst rises temperature. This temperature rise is caused by the release of energy as the ozone is converted back into $O_2$ from a $O_3$. 95% of the energy is released in the first 3 inches. As the gas travels down the pipe to point P it converts nearly all the ozone back to oxygen. The longer the convertor the more perfect the conversion. At C another temperature is taken. The flow is measured by the flow meter D. The point at E outside the converter, the ambient temperature is measured. The measurements from A, C, D, E, and H are sent to the computer I where the measurements are evaluated and the calculation of ozone in % per volume weight is displayed.

The ozone generator can be easily controlled by this simple instrument without the need of UV lights or any wet chemistry. This system is simple, practical, easy to calibrate and inexpensive to produce. This system does two jobs—measures the ozone and destroys it before it is discharged.

To upgrade this catalyst and assure no ozone exists in the "out gas" and to make it a smaller unit, a heater should be installed at point 10-$H^2$. This heater should raise the temperature of the gas that is being acted on up to 500° F. This high temperature will reduce the ozone concentration to near zero, far below the permissable limits.

I claim:

1. An ozone generator comprising first and second electrodes spaced from each other, means for establishing a corona discharge from the first electrode to the second electrode, means for flowing oxygen or an oxygen containing gas at a pressure of 250 to 10,000 psia through said corona discharge area, a first hermetically sealed chamber filled with a first cooling fluid in pressure and heat exchange relation to said first electrode, a second hermetically sealed chamber filled with a second cooling fluid in pressure and heat exchange relation to said second electrode, and flexible barrier means for equalizing or balancing the pressures of the internal cooling fluids and the input gas.

2. The structure of claim 1 in which the first electrode is on a dielectric.

3. The structure of claim 1 in which the second electrode is grounded.

4. The structure of claim 1 in which the first electrode is on a dielectric and grounded.

5. The structure of claim 1 in which the corona forming means is pulses of voltage between said first and second electrodes.

6. The structure of claim 1 further comprising a catalyst platinum or iron oxide on the electrodes to increase the generation of ozone per watt of energy.

7. The structure of claim 5 in which the oxygen containing gas flows through a tube of dielectric material.

8. The structure of claim 7 in which the dielectric material is glass.

9. The structure of claim 1 in which the first and second electrodes are concentric tubes.

10. The structure of claim 1 in which the first and second electrodes are concentric tubes where the inner tube is metal and the outer tube is a dielectric that is coated on its outside with a conductor, this conductor being the second electrode, and the inner metal tube being the first electrode and the high voltage electrode and the second electrode being at ground.

11. The structure of claim 9 in which the electrodes are radially spaced from each other to provide a passageway through which the oxygen or oxygen containing gas flows.

12. The structure of claim 11 in which the hermetically sealed chambers are closed loops having sections of the loops in heat exchange relation to cooling means.

13. The structure of claim 11 having means for applying the pressure of said gas to the liquid of at least one of said loops.

14. The structure of claim 13 further comprising means equalizing the hydraulic pressures of said chambers.

15. The structure of claim 1 in which the first electrode is on the outer surface of a glass tube with opposite ends sealed to the ends or headers of a pressure vessel, an inlet for oxygen or an oxygen containing gas under pressure at one end of the tube and an outlet for ozone at the other end of the tube, the glass tube being subject to bursting pressure of the gas, an annular wall spaced outward from the glass tube and sealed to said headers providing a hermetically sealed chamber for a cooling liquid for said glass tube, and a bellows sealed to said chamber for transmitting pressure from said gas to said cooling liquid for counterbalancing the bursting pressure on the glass tube.

16. The structure of claim 1 in which the first and second electrodes are concentric tubes where the inner tube is metal and the outer tube is a dielectric that is coated on its outside with a conductor, this conductor being the first electrode and the high voltage electrode, and the inner metal tube being the second electrode and at ground.

* * * * *